United States Patent [19]
Silvian

[11] Patent Number: 5,264,843
[45] Date of Patent: Nov. 23, 1993

[54] HIGH SPEED REFLECTED IMPEDANCE TELEMETRY SYSTEM FOR IMPLANTABLE MEDICAL DEVICE

[75] Inventor: Sergiu Silvian, La Crescenta, Calif.

[73] Assignee: Siemens Pacesetter, Inc., Sylmar, Calif.

[21] Appl. No.: 665,627

[22] Filed: Mar. 5, 1991

Related U.S. Application Data

[63] Continuation of Ser. No. 333,497, Apr. 5, 1989, abandoned.

[51] Int. Cl.$^5$ ............................................. G08C 19/02
[52] U.S. Cl. ..................... 340/870.18; 340/870.26; 340/870.4; 340/870.42; 340/870.28; 128/903
[58] Field of Search ............... 340/870.18, 870.19, 340/870.26, 870.39, 870.42, 870.28, 870.31; 128/419 PT, 696, 903; 335/1 R, 15.02

[56] References Cited

U.S. PATENT DOCUMENTS

| | | | |
|---|---|---|---|
| 2,567,286 | 9/1951 | Hugenholtz | 331/15 |
| 4,083,237 | 4/1978 | Levesque | 340/870.42 |
| 4,151,463 | 4/1979 | Kibler | 331/2 |
| 4,223,679 | 9/1980 | Schulman et al. | 128/419 PT |
| 4,281,664 | 8/1981 | Duggan | 340/870.26 |
| 4,453,162 | 6/1984 | Money et al. | 340/870.39 |
| 4,847,617 | 7/1989 | Silvian | 340/870.39 |

Primary Examiner—Donald J. Yusko
Assistant Examiner—Michael Horabik
Attorney, Agent, or Firm—Leslie S. Miller

[57] ABSTRACT

A telemetry system which will transmit data at a relatively high rate while retaining a high degree of accuracy is disclosed which utilizes a servo feedback loop in conjunction with a conventional reflected impedance receiving front end parallel LC circuit, an AM demodulator, and an oscillator to drive the LC circuit at a desired frequency. The feedback loop operates to keep the voltage across the LC circuit constant over time, and does not affect short term variations in the voltage across the LC circuit which are caused by the variations in the reflected impedance. While frequency response of the system without the loop declines from a maximum value at zero frequency, the frequency response of the system of the present invention with the loop is shifted which permits data transmission at a substantially higher rate.

13 Claims, 4 Drawing Sheets

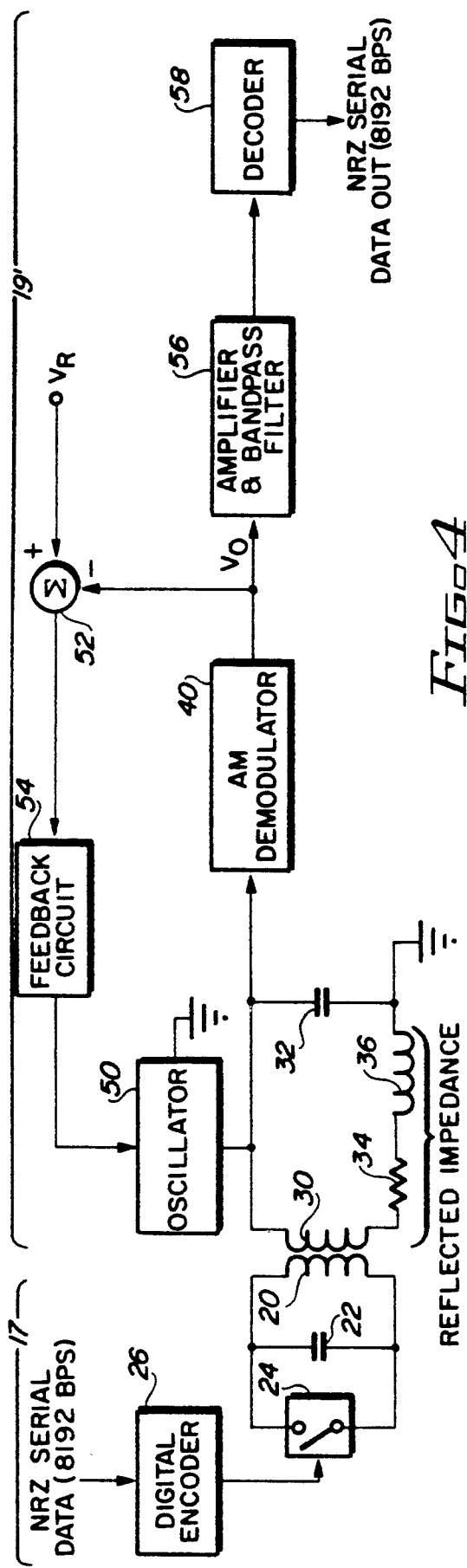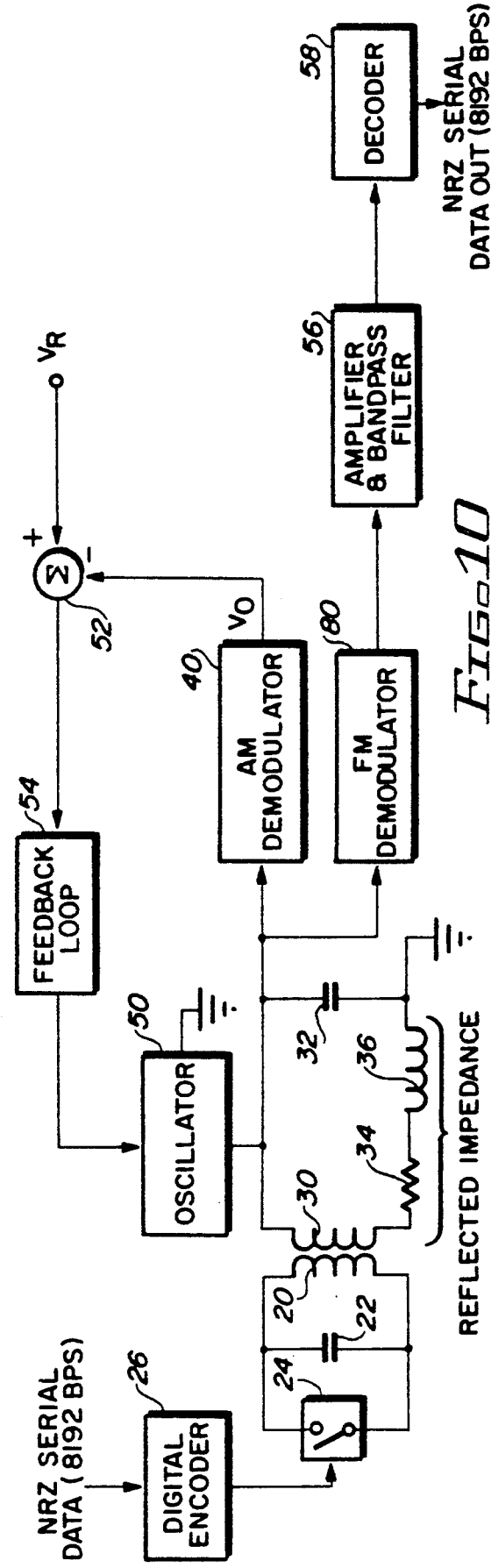

HIGH SPEED REFLECTED IMPEDANCE TELEMETRY SYSTEM FOR IMPLANTABLE MEDICAL DEVICE

This application is a continuation of application Serial No. 07/333,497, filed Apr. 5, 1989, now abandoned.

BACKGROUND OF THE INVENTION

1. Field of the Invention

The present invention relates generally to implantable medical devices, and more particularly to a telemetry system for use in medical devices of various types and for various purposes implantable within the human body. Even more particularly, the present invention provides a telemetry system which will transmit data at a relatively high rate between an implanted medical device and an external device while retaining a high degree of accuracy.

With the ever-shrinking size of electronic circuitry, the implantation into the human body of electronic medical devices has become more and more common. Although the most commonly known of such devices is the cardiac pacemaker, there are a variety of devices which are implanted into the human body, including devices for the stimulation or sensing, or both, of the brain, nerves, the spinal cord, muscles, bones, glands, or other body organs or tissues.

It will be appreciated by those skilled in the art that such implantable devices are becoming increasingly complex, and that more functions can be crammed into a relatively smaller electronic chip or circuit. Implantable medical devices have used bidirectional telemetry for a number of years. Information transmitted between the implanted device and an external transceiver may include, for example, device identification information, biological data, current operational parameters of the device, technical information regarding proper operation of the device, battery charge condition, revised operational parameters (programming information) for the device, and verification of information transmitted between the implanted device and the external transceiver.

With an ever-increasing amount of data being processed and available within the implantable device, there has been a corresponding increase in the need to transmit more data from the implanted device to the external transceiver for analysis, reprogramming of the implantable device, or other purposes. The need for more data to be transmitted in both directions has increased tremendously the amount of time required both to interrogate the implanted device and to reprogram the implanted device. An upper limit on the amount of data flowing between the implanted device and the external transceiver has therefore become directly proportional to the amount of time which may reasonably be taken to interrogate and reprogram the implanted device.

Accordingly, it is desirable to achieve a higher rate of data transfer between the implanted device and the external transceiver to eliminate this artificial impediment and to maximize the communication between the implanted device and the external transceiver. Of course, an increase in the rate of data exchange may not be obtained at the expense of accuracy in a medical device, particularly if the device is a life-sustaining device such as a pacemaker. Absolute accuracy is required, and it is apparent that an increase in the rate of data transfer will be nullified by an increase in the amount of time spent to verify data to ensure the degree of accuracy required.

The recent development of LSI circuits incorporating low current analog-to-digital converters has made the use of such converters in implantable devices possible. There are, of course, limitations surrounding the design of new implantable systems or portions thereof, the most limiting of which is the consumption of energy by the system. Implanted systems are customarily powered by a long-lasting non-replaceable internal battery, and the current consumption of a telemetry sub-system thus becomes perhaps the most important design factor to be considered.

Previously known devices have established various methods of communicating non-invasively through the skin. For example, U.S. Pat. No. 4,223,679, to Schulman et al., which patent is assigned to the assignee of the present invention, shows an implanted device which uses little or no current to transmit information by relying on reflected impedance of an internal L-C circuit. Internal modulation circuits in the implanted device transmit digital or analog data by modulating the reflected impedance, and the external transceiver utilizes an oscillator having varying frequency and amplitude outputs determined by a coupled RF magnetic field carrier to an L-C circuit in the external transceiver. This system works well, but, unfortunately, has speed limitations making it unsuitable for transmitting the amount of information contemplated herein.

Another type of device uses an active type transmitter, with the transmitted energy being taken from the implantable device battery. This type of device, which is illustrated in U.S. Pat. No. 4,281,664, to Duggan, has a data rate which is limited to approximately 100 BPS (bits per second). Another device which utilizes an active type transmitter is shown in U.S. Pat. No. 4,453,162, to Daly et al. The Daly et al. device can not achieve more than 0.25 to 0.05 bps/carrier cycle, a rate too low for the applications contemplated herein.

Still another telemetry system is disclosed in my U.S. Pat. No. 4,681,111, which increases the speed of the device disclosed in above-referenced U.S. Pat. No. 4,223,679. U.S. Pat. No. 4,681,111 is hereby incorporated herein by reference. However, the maximum rate of this device is still limited by the bandwidth of the external device L-C oscillator. Those skilled in the art will also appreciate that it is not practical to increase the carrier frequency above approximately eight kHz, since the metal enclosure of the implanted device will experience eddy currents great enough to attenuate the signal significantly. In addition, increasing the carrier frequency makes electromagnetic interference from video display terminals, which are generally approximately 16 kHz, a significant problem. Consequently, techniques requiring a number of carrier cycles for each signal bit will be capable of achieving a speed of only two to four kBPS.

One possible solution is disclosed in my U.S. Pat. No. 4,847,617, which patent is hereby incorporated herein by reference. This system utilizes both in-phase and quadrature data components, and frequency modulates both data components into a single transmitted sinusoidal signal which varies in frequency between two selected frequencies. The signal is received and decoded, preferably by a coherent decoder, into in-phase and quadrature components, which are then integrated and sampled to produce the two transmitted in-phase and quadrature data components, which may then be recombined to produce the transmitted data. The system requires only low power, and is capable of operating at a relatively high data rate while retaining a high degree of accuracy due to the splitting of the signal into the in-phase and quadrature data components.

It will, however, be appreciated that there exists a substantial need for other telemetry systems which are capable of accurately transmitting and receiving data at a rate enabling the substantial amounts of data used by current implantable systems to be conveniently sent in a relatively short period of time. The amount of power required by the implanted portion of such a system must be minimal, so as not to adversely affect battery life. The system should be compact so as to not add significantly to the space required by the implanted device. Finally, it is also an objective that all of the aforesaid advantages and objectives be achieved without incurring any substantial relative disadvantage.

SUMMARY OF THE INVENTION

The disadvantages and limitations of the background art discussed above are overcome by the present invention. With this invention, a servo loop is added to a conventional reflected impedance receiving front end circuit using an AM demodulator. Such a circuit typically has an external inductor in parallel with a capacitor to tune the inductor to an implanted inductor from which information is being transmitted. The AM demodulator is connected across the parallel LC combination. An oscillator is used to drive the LC circuit at a desired frequency.

The present invention adds a servo loop between the output of the AM demodulator and the oscillator. The feedback loop compares the voltage output from the AM demodulator with a reference voltage, and thus operates to keep the voltage across the LC circuit constant over time. The feedback loop does not affect short term variations in the voltage across the LC circuit which are caused by the variations in the reflected impedance since the data transmission frequency possible with the system of the present invention is relatively high.

The frequency response of the system of the present invention is thus tailored to the desired response required by a high speed telemetry channel. Mainly, the system frequency response (the response to the implanted device modulation), specified as center frequency and bandwidth, can be specified independently of the L-C oscillator parameters through use of the servo loop. While frequency response of the system without the loop declines from a maximum value at zero frequency, the frequency response of the system of the present invention with the loop is shifted which in turn will permit transmission at a substantially higher data rate.

An amplifier and bandpass filter is driven by the output of the AM demodulator, with the output from the amplifier and bandpass filter driving a decoder. Alternately, an FM demodulator may be used in addition to the AM demodulator to demodulate the signal before it is supplied to the amplifier and bandpass filter and the decoder. The AM demodulator, however, remains in the circuit and is still used as an integral part of the servo loop.

Thus, the system of the present invention is capable of accurately transmitting and receiving data at a high rate. The amount of power required by the implanted portion of such a system is based on the energy provided by the external device and the implanted device has to provide only minimal power, and as such the system of the present invention does not adversely affect battery life. The system is compact so as to not add significantly to the space required by the implanted device. Finally, all of the aforesaid advantages and objectives are achieved without incurring any substantial relative disadvantage.

DESCRIPTION OF THE DRAWINGS

These and other advantages of the present invention are best understood with reference to the drawings, in which:

FIG. 4 is a functional schematic of a high speed reflected impedance telemetry system constructed according to the teachings of the present invention;

FIG. 10 is a functional schematic of a high speed reflected impedance telemetry system similar to that shown in FIG. 4, but with an FM demodulator being used in addition.

DETAILED DESCRIPTION OF THE PREFERRED EMBODIMENT

Figure 1:
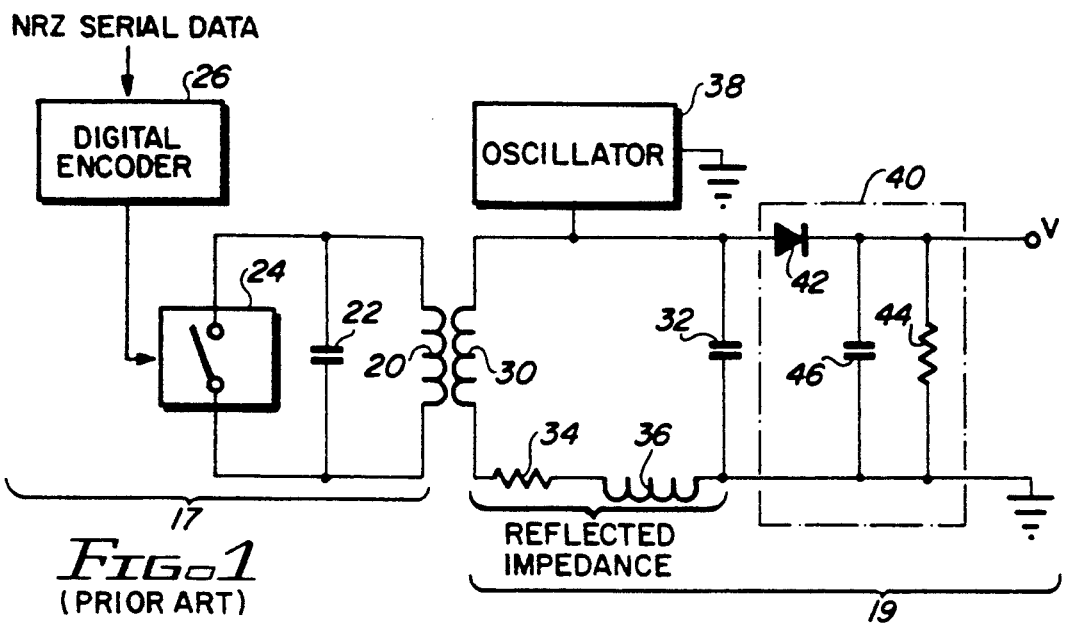
FIG. 1 is a functional schematic of a known reflected impedance telemetry system used with an AM demodulator in the receiving end.

Before discussing the preferred embodiment of the present invention, it is useful to examine a known reflected impedance telemetry system to determine its shortcomings. Such a system is illustrated in FIG. 1, which shows both the implanted portion 17 and the external portion 19 of such a system. An inductor or coil 20 is tuned to a resonant frequency $f_0$ by a capacitor 22 which is connected in parallel across the inductor 20. Also connected in parallel across the inductor 20 and the capacitor 22 is a low impedance semiconductor switch 24, which is typically a CMOS device.

The external receiver used to receive data transmitted from the implanted device has a coil or inductor 30 which is applied to the surface of the skin over the location of the inductor 20 of the implanted device. The two inductors 20 and 30 are constructed in a manner whereby they will magnetically couple to each other. As such, they may be regarded as two coils of a transformer having a low coupling coefficient. A capacitor 32 is connected across the inductor 30.

With the switch 24 open, the circuit will oscillate at the frequency $f_0$ in an essentially sinusoidal manner, with a sinusoidal voltage $V_L$ across the inductor 20 and the capacitor 22. In this state, the circuit will dissipate energy taken from the external tank circuit including the inductor 30 and the capacitor 32. When the switch 24 is closed, the inductor 20 and the capacitor 22 are shorted. In this state, the circuit will dissipate lower energy taken from the external tank circuit including the inductor 30 and the capacitor 32. Accordingly, by opening and closing the switch 24, the voltage on the capacitor 32 is AM and FM modulated.

Non-return-to-zero (NRZ) serial binary data is supplied by the implanted device to a digital encoder 26, which is used to open and close the switch 24 to modulate the voltage signal across the inductor 20. In the example used herein, an NRZ data bit of "0" is encoded by the digital encoder 26 to be two excursions from zero to one or from one to zero, while an NRZ data bit of "1" is encoded by the digital encoder 26 to be a single excursion from zero to one or from one to zero (see FIG. 9).

A reflected impedance from the implanted circuit appears in series with the inductor 30 and the capacitor 32. The reflected impedance is illustrated in FIG. 1 by a resistor 34 and an inductor 36 connected in series together with the inductor 30 and the capacitor 32. When the switch 24 is open, the resistance of the resistor 34 is high, and when the switch 24 is closed, the resistance of the resistor 34 is very low, near zero. When the switch 24 is opened, the inductance of the inductor 36 will have a low negative value, and while the switch 24 is closed the inductor 36 will have approximately zero inductance.

An oscillator 38 is connected to the tuned external circuit, and oscillates approximately at $f_0$. As such, the inductor 30 and the capacitor 32 will oscillate at a frequency which is approximately $f_0$. Generally, the inductor 30 and the capacitor 32 are tuned to $f_0$ to accomplish an efficient transfer of energy. The oscillator 38 may be a Colpitts circuit, or the circuit shown in FIG. 2 in U.S. Pat. No. 4,233,679, to Schulman.

As the switch 24 is opened and closed, the voltage amplitude across the capacitor 32 will change, as will the frequency of oscillation. When the switch 24 is opened, the voltage across the capacitor 32 will drop due to an increase in reflected resistance, and the frequency of oscillation will increase slightly. Therefore, it is apparent that as the switch 24 is opened and closed, the voltage across the capacitor 32 will be modulated. In addition, the main frequency of oscillation of the circuit in the external device, which is $f_0$, will be modulated somewhat by the switch 24 being opened and closed.

It will therefore be appreciated that the modulation imposed by the switch 24 on the implanted tuned circuit will appear across the capacitor 32. Accordingly, a demodulator may be used to obtain the data being transmitted. In the circuit shown in FIG. 1, an AM demodulator 40 is used. The AM demodulator 40 will extract the AM modulation produced by the reflected impedance, with the output $V_o$ of the AM demodulator 40 containing the DC oscillator amplitude plus the AC modulation.

The AM demodulator 40 may typically be a diode 42 having its anode connected to the ungrounded side of the capacitor 32, with its cathode being the output of the circuit at which $V_o$ appears. A resistor 44 and a capacitor 46 are connected together in parallel between the cathode of the diode 42 and ground. It will of course be recognized by those skilled in the art that there are various other AM demodulator designs, and any of them could alternatively be used.

Typically an amplifier and band pass filter (not shown) may then be used to filter out the carrier frequency, thus extracting, amplifying and band limiting the modulating AC signal. Thus, only the frequency portion of the signal necessary to reconstruct the transmitted data is passed on. A decoder (not shown), is then used to decode the signal to provide the original transmitted data.

The most important characteristic of the system shown in FIG. 1 is its maximum data rate. Consider for the moment that the digital encoder 26 is removed from the circuit of FIG. 2, and that the NRZ serial data is applied directly to the switch 24. The AM modulation used is typically a double sideband type, since both sidebands are transmitted, and the frequency spectrum of the NRZ serial data itself is infinite. For a binary communication to be placed, the system bandwidth must be larger than the minimum Nyquist rate of $1/2T = 0.5 f_r$, where T is the bit duration and $f_r$ is the bit rate.

Figure 2:
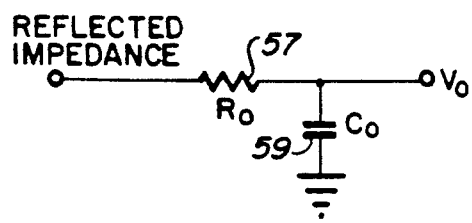
FIG. 2 illustrates the baseband equivalent to the circuit shown in FIG. 1.

From practical considerations, generally the bandwidth is not smaller than $0.75 f_r$. A double sideband AM modulation will thus require at least a $1.5 f_r$ bandwidth. The oscillator 38, the inductor 30, and the capacitor 32 are equivalent to a 2-pole bandpass filter which passes the AM modulation on the $f_o$ carrier. FIG. 2 illustrates the baseband equivalent to the circuit of FIG. 1. In FIG. 1, a resistor 57 has one side as the input to the circuit, with the input being the reflected impedance. The other side of the resistor 57 is the output of the circuit on which $V_o$ appears. Connected across the output of the circuit and ground is a capacitor 59.

Figure 3:
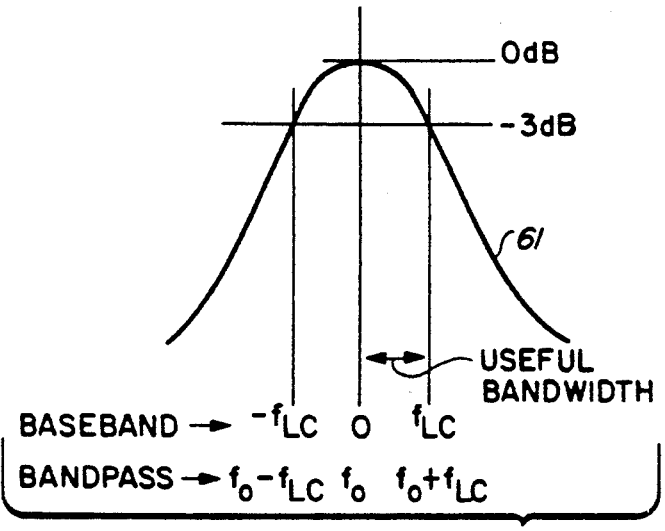
FIG. 3 shows the frequency response limitations of the system shown in FIG. 1.

FIG. 3 shows the frequency response of the system shown in FIG. 1 (which response is indicated by the reference numeral 61). At baseband (after AM demodulation), and assuming the AM demodulator to be perfect with no modulation frequency alteration, the system is equivalent to a one-pole lowpass filter having a bandwidth $f_{LC}$. The width of this bandwidth $f_{LC}$ is limited by the coil quality of factor Q as defined by the formula:

$$f_{LC} = \frac{1}{2} \frac{f_0}{Q} = \frac{1}{2\pi R_0 C_0}. \tag{1}$$

In practice, the maximum rate at which transmitted data may be accurately received will be $f_{LC}$, since at frequencies above $f_{LC}$ the amplitude of the signal will have dropped more than 3 dB. Accordingly, the maximum rate of transmission of data will be $f_{LC}$, which for the system shown in FIG. 1 is only approximately 400 Hz. This effectively limits the rate of data transmission to a relatively low rate.

Referring now to FIG. 4, a system illustrating the preferred embodiment of the present invention is shown. The implanted portion 17 of the system is identical to the system of FIG. 1 and there are other similarities in the external portion 19' of the system. The system of FIG. 4 uses the inductor 30 which is applied to the surface of the skin over the location of the inductor 20 of the implanted device to couple the two inductors 20 and 30 magnetically to each other. The capacitor 32 is connected across the inductor 30, with the reflected impedance from the implanted circuit being the resistor 34 and the inductor 36.

The system of FIG. 4 also uses an oscillator 50 which is connected to the tuned external circuit, and which will oscillate approximately at $f_0$. The inductor 30 and the capacitor 32 are again tuned to $f_0$ to accomplish an efficient transfer of energy. Again, as the switch 24 is opened and closed, the voltage and frequency across the capacitor 32 will be modulated.

Accordingly, a demodulator may be used to obtain the data being transmitted, and the AM demodulator 40 is again used. The AM demodulator 40 will extract the AM modulation produced by the reflected impedance, with the output $V_o$ of the AM demodulator 40 containing the DC oscillator amplitude plus the AC modulation. The circuit of FIG. 4 differs from the circuit of FIG. 1 in that a feedback loop is used between the output $V_o$ of the AM demodulator 40 and the oscillator 50 which is used to drive the external circuit.

A comparator 52 is used to compare the AM demodulator 40 output $V_o$ with a reference voltage $V_R$. The output of the comparator 52 is supplied to a feedback circuit 54, the output of which is used to drive the oscillator 50. The feedback loop will thus operate to keep the voltage amplitude across the capacitor 32 constant over time. It must be noted at this point that the feedback loop will not affect short term variations in the voltage amplitude across the capacitor 32 which are caused by the variations in the reflected impedance caused by the switch 24 being opened and closed. This is so since the frequency at which the switch 24 is opened and closed is relatively high, as will become evident below.

Also connected to the output of the AM demodulator 40 is an amplifier and bandpass filter 56, which is used to amplify and filter the signal from the AM demodulator 40. Finally, a decoder 58 is used to decode the amplified and filtered signal to obtain the original data. The amplifier and bandpass filter 56 and the decoder 58 are of standard design and are well known in the art.

Figure 5:
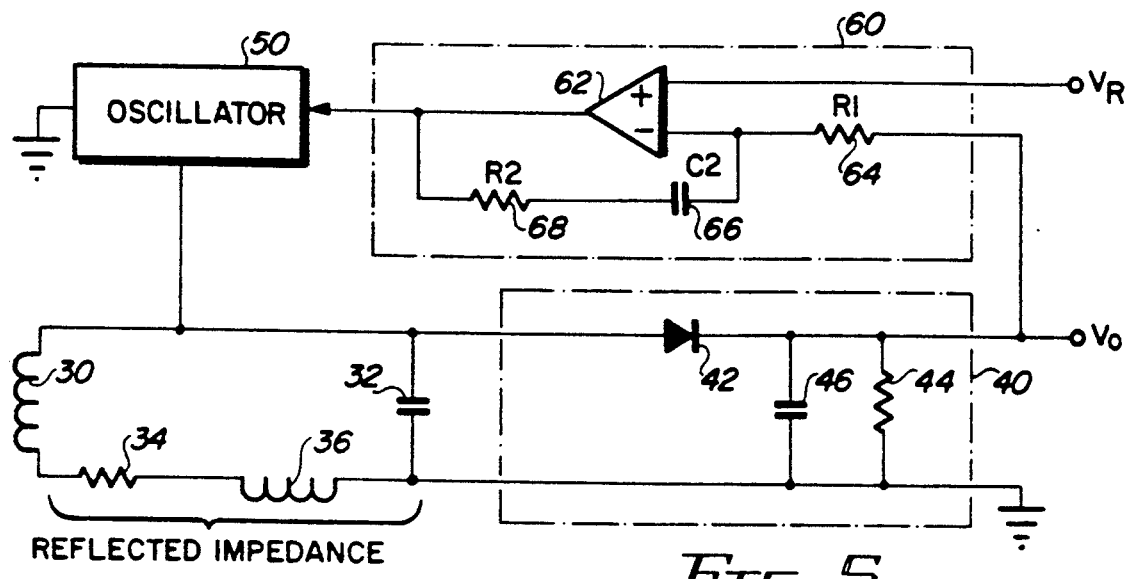
FIG. 5 illustrates the high speed front end of the receiver of the telemetry system shown in FIG. 4, with an AM demodulator being used in conjunction with a closed servo loop feedback circuit driving the oscillator.

Referring next to FIG. 5, a circuit 60 which will perform the functions of the comparator 52 and the feedback circuit 54 is shown. In this circuit 60, an operational amplifier 62 is shown which is connected as an integrator. The reference voltage $V_R$ is connected to the positive input of the operational amplifier 62. A resistor 64 is connected between the output $V_o$ of the AM demodulator 40 and the negative input of the operational amplifier 62. A capacitor 66 is connected on one side to the negative input of the operational amplifier 62, and on the other side to one side of a resistor 68. The other side of the resistor 68 is connected to the output of the operational amplifier 62.

To complete the feedback loop, the output of the operational amplifier 62 is connected to the oscillator 50. The output from the operational amplifier 62 will keep the voltage output from the oscillator 50 constant over time, as mentioned above. This feedback loop has two essential effects. The first of these effects is that the amplitude of the output from the oscillator 50 will be such that the DC output from the AM detector 40 will be constant, equal to $V_R$.

Figure 6:
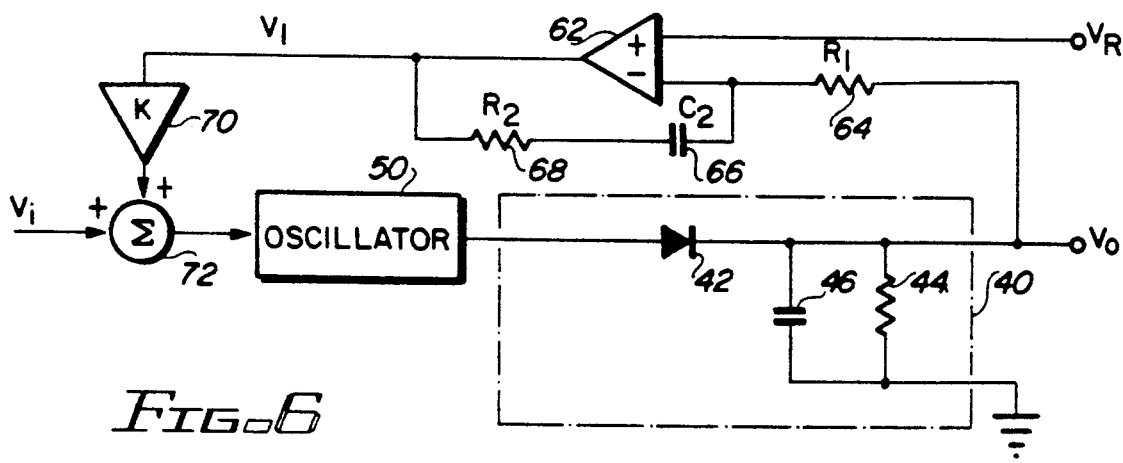
FIG. 6 illustrates the bandpass equivalent to the circuit shown in FIG. 5.

The second effect of the feedback loop is that the transfer function from the reflected impedance modulation to the output $V_o$ of the AM demodulator 40 will no longer be a 1-pole lowpass response, but rather a bandpass response. The bandpass equivalent of the circuit shown in FIG. 5 is shown in FIG. 6. The output from the operational amplifier 62 is connected to drive an amplifier 70. A coefficient K is equal to the derivative of $V_o$ divided by the derivative of $V_1$. The output of the amplifier 70 is supplied as an input to a summer 72, the other input of which is the external modulation $V_i$ caused by the variations in the reflected impedance. The output of the summer 72 drives the oscillator 50.

Figure 7:
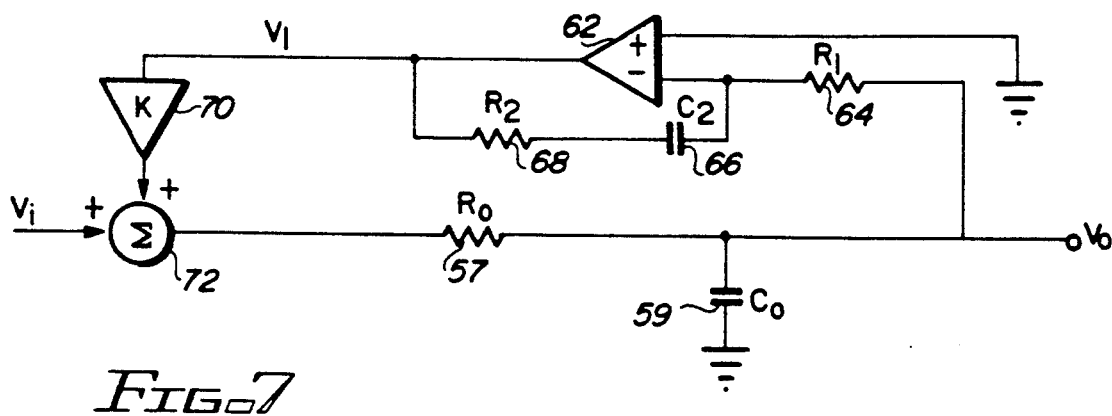
FIG. 7 illustrates the baseband equivalent to the circuit shown in FIG. 6.

Taking the lowpass baseband equivalent of the circuit shown in FIG. 6, we obtain the circuit of FIG. 7. The positive input of the operational amplifier 62 is grounded. Accordingly, the output of the summer 72 is supplied to the one side of the resistor 57, with the other side of the resistor 57 being the output $V_o$. The capacitor 59 is connected across the output $V_o$ and ground. The resistor 57 and the capacitor 59 make up a one pole low pass filter equivalent to the one shown in FIG. 2.

By performing the following elementary control loop calculations, the determination of an overall input-output transfer function H(s) may be made:

$$H(s) = \frac{V_o}{V_i} \tag{2}$$

$$w_{LC} = 2\pi f_{LC} = \frac{1}{R_o C_o} \tag{3}$$

$$H_{LC} = \frac{1}{1 + \frac{s}{w_{LC}}} \tag{4}$$

$$\frac{V_o}{V_i} = \frac{H_{LC}}{1 - H_{LC} H_f} = H(s) \tag{5}$$

$$H_f = -K \frac{1 + R_2 C_2 s}{R_1 C_2 s} \tag{6}$$

$$H(s) = \frac{w_{LC} s}{s^2 + \frac{R_1 + K R_2}{R_1} w_{LC} s + K \frac{w_{LC}}{R_1 C_2}} \tag{7}$$

$$w_{obp} = \sqrt{K \frac{w_{LC}}{R_1 C_2}} \tag{8}$$

$$Q = \frac{R_1}{R_1 + K R_2} \frac{w_{obp}}{w_{LC}} \tag{9}$$

Figure 8:
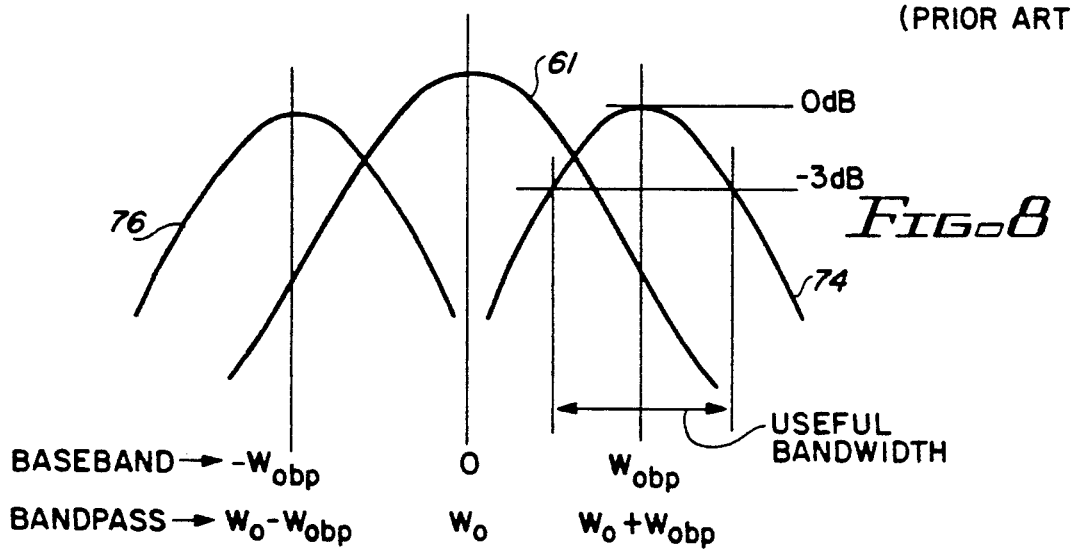
FIG. 8 shows the system frequency response of the circuit shown in FIG. 5.

By inspection, it may be seen that H(s) is a standard 2-pole bandpass response having a center frequency $w_{obp}$ and a Quality factor Q which may be tailored to the application, and which are no longer solely determined by the oscillator L-C elements. FIG. 8 illustrates how the new frequency response (indicated by the reference numerals 74 and 76) appears compared to the L-C response of the system of FIG. 1 (indicated by the reference numeral 61, which response was also illustrated in FIG. 3).

As may be seen from the H(s) relation (equation 7) above and from FIG. 8, the system response 74 of the system shown in FIG. 4 at zero frequency is zero as opposed to maximum in the systems of FIG. 1. The system response 74 instead is centered around the frequency $w_{obp}$, and the useful bandwidth is substantially wider than the useful bandwidth of the system of FIG. 1.

Referring for the moment to FIG. 4, the digital encoder 26 has the task of changing the frequency spectrum from NRZ (non-return-to-zero), which has components down to DC, into a spectrum which contains no components close to zero frequency. In the preferred embodiment of the present invention, an MSK (minimum-shift-keying) encoder is used which has a first frequency $f_1$ which is 8192 Hz, and a second frequency $f_2$ which is 4096 Hz. In the preferred embodiment, there is a straight coding rule in which a zero will be transmitted as $f_1$ and a 1 will be transmitted as $f_2$, as shown in FIG. 9.

Figure 9:
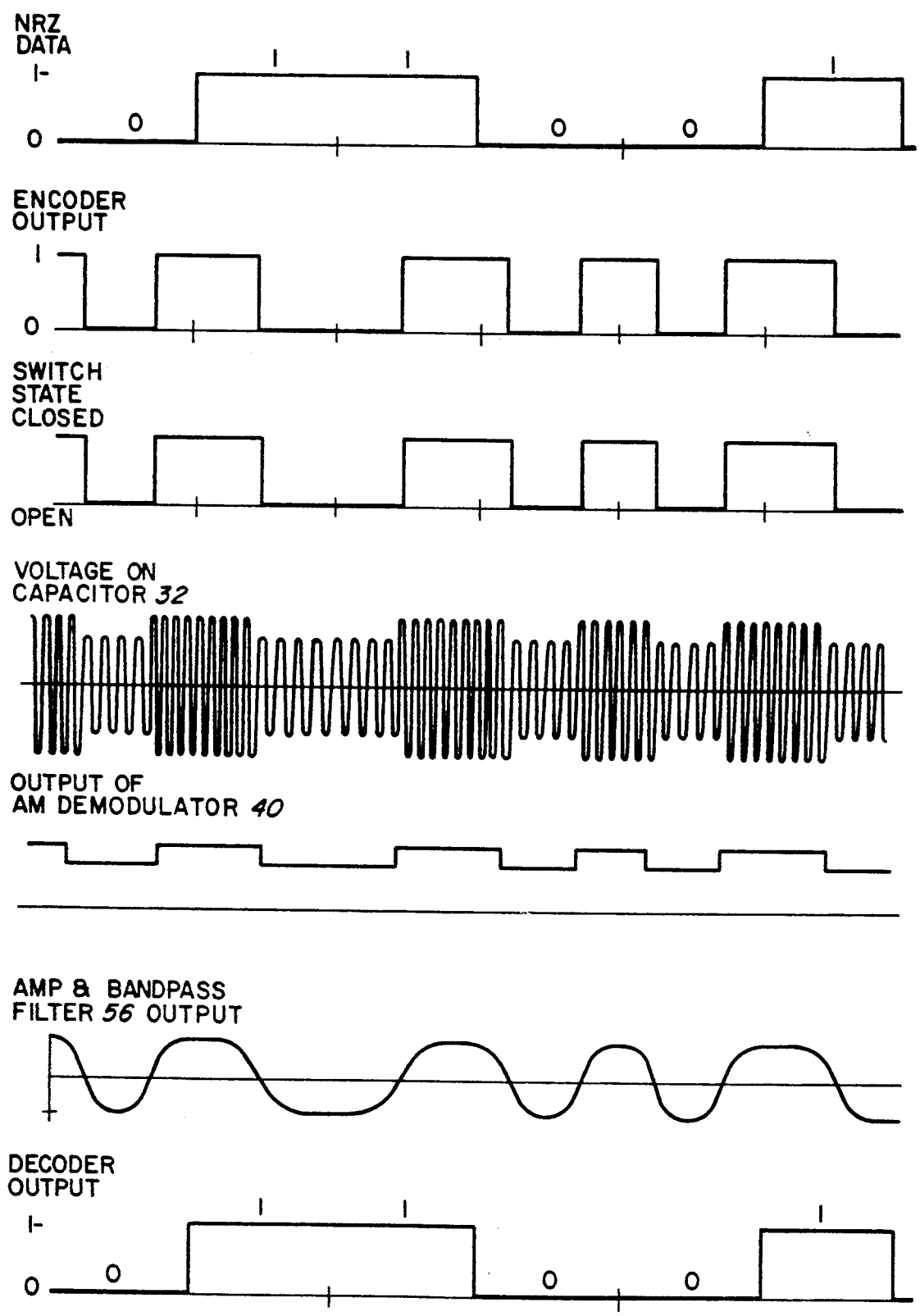
FIG. 9 shows selected signals in the transmitter and receiver.

The voltage across the capacitor 32 is shown in FIG. 9, with the associated output from the AM demodulator 40, which is one side of the voltage across the capacitor 32. The amplifier and bandpass filter 56 produces a signal responsive to the non-DC portion of the envelope of the output from the AM demodulator 40. The signal output of the amplifier and bandpass filter 56 will then be used by the decoder 58 to decode the signal back to NRZ.

Construction of the decoder 58 will be apparent to one skilled in the art. An MSK encoding is known to require a relatively low transmission bandwidth. In fact, it can work on a two-sided bandwidth of 0.7 divided by the period T. This results in the factor 0.7 being multiplied by the frequency 8192 Hz to obtain a 5734 Hz bandwidth which is centered on $f_{obp}$ of (8192+4096)/2, or 6144 Hz.

The choice of $f_1$ and $f_2$ can lead to simplification of the decoder 58. The best decoder performance will be obtained using a coherent decoder which, using a PLL (phase-locked-loop), regenerates at the receiver the two carriers $f_1$ and $f_2$, as well as the bit clock timing. However, here the bit clock is equal to $f_1$ and $f_2=\frac{1}{2}f_1$, so the carriers may be obtained very simply. A non-coherent decoder could also be used, with reduced performance but with simplified circuits. Detailed circuit schematics for the digital encoder 26, the amplifier and bandpass filter 56, and the decoder 58 are not presented since they may be implemented in a multitude of ways well known to persons skilled in the art.

Referring next to FIG. 10, it should be noted that while the AM demodulator 40 is necessarily contained in the loop, an FM demodulator 80 could also be connected with its input across the capacitor 32. The output of the FM demodulator 80 would then drive the amplifier and bandpass filter 56.

It should also be noted that such telemetry systems typically have provisions to work in the opposite direction, that is from the external device to the implanted device. In this case, a receiver detector would be connected across the inductor 20.

It may therefore be appreciated from the above detailed description of the preferred embodiment of the present invention that it is capable of accurately transmitting and receiving data at a high rate. The amount of power required by the implanted portion of such a system is minimal, and as such does not adversely affect battery life. The system is compact so as to not add significantly to the space required by the implanted device. Finally, all of the aforesaid advantages and objectives are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A high speed reflected impedance telemetry system for use with an implantable medical device comprising:
   an implantable medical device that includes means for performing a specified medical function;
   an external transceiver; and
   bidirectional data telemetry means for transmitting data between said implantable medical device and said external transceiver, said bidirectional data telemetry means including:
   generating means within one of said implantable medical device or said external transceiver for generating an information-containing magnetic field;
   receiving means within the other of said implantable medical device or said external transceiver for receiving and demodulating said information-containing magnetic field, and for establishing a wide bandwidth between said implantable medical device and said external transceiver, said receiving means comprising:
   a first inductor for receiving said information-containing magnetic field,
   a first capacitor connected in parallel across said first inductor,
   an oscillator connected to drive said first inductor and said first capacitor with an oscillating output signal,
   demodulator means connected across said first inductor and said first capacitor, said demodulator means having an output, and
   feedback loop means connected from the output of said demodulator means to said oscillator for controlling the amplitude of said oscillating output signal so as to widen the bandwidth through which information may be transferred between said implantable medical device and said external transceiver,
   whereby a high rate of change of said information-containing magnetic field may occur within said wide bandwidth, whereby a high data rate transfer of information may occurs between said implantable medical device and said external transceiver.

2. The system as set forth in claim 1, wherein said generating means includes:
   a second inductor;
   a second capacitor connected in parallel across said second inductor;
   switch means for selectively connecting a low impedance or a high impedance across said second inductor and said second capacitor, said low impedance comprising a closed state of said switch means, and said high impedance comprising an open state of said switch means; and
   encoding means for opening and closing said switch means in accordance with desired serial data to be transferred between said implantable medical device and said external transceiver device.

3. The system as set forth in claim 2, wherein said second inductor is magnetically coupled to said first inductor when information is transferred between said implantable medical device and said external transceiver device.

4. The system as set forth in claim 3, wherein said first inductor and said first capacitor have values to tune them to a frequency $f_0$, and said oscillator is set to oscillate at a frequency which is approximately $f_0$, and further wherein said second inductor and said second capacitor also have values to tune them to frequency $f_0$.

5. The system as set forth in claim 4, wherein said feedback loop means comprises:
   an operational amplifier having a positive input, a negative input, and an output, said positive input of said operational amplifier being supplied with a DC reference voltage;
   a first resistor connected between the output of said demodulator means and said negative input of said operational amplifier;
   a third capacitor having a first terminal and a second terminal, said first terminal of said third capacitor being connected to said negative input of said operational amplifier; and
   a second resistor having a first terminal and a second terminal, said first terminal of said second resistor being connected to said second terminal of said third capacitor, said second terminal of said second resistor being connected to the output of said operational amplifier, the output of said operational amplifier also being connected to drive said oscillator.

6. The system as set forth in claim 4, wherein said demodulator means comprises an AM demodulator.

7. The system as set forth in claim 6, further including:
   an FM demodulator connected across said first inductor and said first capacitor, said FM demodulator having an output;
   an amplifier and bandpass filter having as an input the output from said FM demodulator, said amplifier and bandpass filter providing an output; and
   a decoder having as an input the output from said amplifier and bandpass filter.

8. A bidirectional telemetry system for transferring data between an implantable medical device and an external transceiver device, comprising:
   transmitting means within one of said implantable medical device or said external transceiver device for generating an information-containing magnetic field in accordance with said data being transferred; and
   receiving means within the other of said implantable medical device or said external transceiver device for receiving and demodulating said information-containing magnetic field in order to obtain the data being transferred;
   said transmitting means including:
      a first inductor for transmitting said information-containing magnetic field,
      a first capacitor connected in parallel across said first inductor,
      a switch connected in parallel across said first inductor and said first capacitor, and
      means responsive to said data being transferred for periodically, sequentially opening and closing said switch to modulate a voltage across said first inductor and said first capacitor;
   said receiving means including:
      a second inductor for receiving said information-containing magnetic field,
      a second capacitor connected in parallel across said second inductor,
      an oscillator connected to drive said second inductor and said second capacitor,
      said second inductor, second capacitor and oscillator causing said telemetry system to assume a first bandwidth,
      an AM demodulator connected across said second inductor and said second capacitor, said AM demodulator having an output containing an AC component and a DC component, and
      feedback loop means connected from the output of said AM demodulator to said oscillator, said feedback loop means for maintaining the DC component of the output of said AM demodulator constant and for further causing said telemetry system to assume a second bandwidth, said second bandwidth being wider than said first bandwidth;
   whereby a higher rate of change of said information-containing magnetic field may occur through said second bandwidth than could occur through said first bandwidth, and hence a higher data rate transfer may be achieved between said generating means and said receiving means.

9. The bidirectional telemetry system, as set forth in claim 8, wherein said means for periodically, sequentially opening and closing said switch in said transmitting means comprises a digital encoder that closes and opens said switch in accordance with a desired data modulation pattern of the data being transferred.

10. The bidirectional telemetry system, as set forth in claim 9, wherein said desired data modulation pattern comprises a non-return-to-zero (NRZ) data format wherein an NRZ data bit of "0" is represented as two excursions from a first voltage signal level to a second voltage signal level, and an NRZ data bit of "1" is represented to be a single excursion from the first voltage signal level to the second voltage signal level.

11. In an implantable medical device coupled to an external transceiver, an improved reflected impedance telemetry system for transmitting data at a high rate between the implantable medical device and the external transceiver; a first of said implantable medical device or said external transceiver including means for generating an information-containing magnetic field, and a second of said implantable medical device or said external transceiver including means for sensing said information-containing magnetic field and generating a demodulated signal representative of the information contained therewithin; said means for sensing said information-containing magnetic field including a first inductor adapted to be magnetically coupled to said information-containing magnetic field, a first capacitor connected in parallel across said first inductor, an oscillator connected to drive said first inductor and said first capacitor at a frequency $f_0$, and an AM demodulator connected across said first inductor and said first capacitor, said AM demodulator generating said demodulated signal, said demodulated signal containing an AC component and a DC component; said first inductor, first capacitor and oscillator providing a first bandwidth that permits the information contained within said information-containing magnetic field to be detected up to a first data transfer rate; the improvement comprising:
   a feedback loop circuit that connects the demodulated signal of said AM demodulator to said oscillator, said feedback loop circuit causing the DC component of the demodulated signal of said AM demodulator to be maintained substantially constant, and said feedback loop means also providing a second bandwidth wider than said first bandwidth that permits the information contained within said information-containing magnetic field to be detected up to a second data transfer rate, said second data transfer rate being greater than said first data transfer rate;

whereby information contained within said information-containing magnetic field may be transferred between said implantable medical device and said external transceiver at a higher data transfer rate than is possible without said feedback loop circuit.

12. The improved reflected impedance telemetry system for use between an implantable medical device and an external transceiver, as set forth in claim 11, wherein said feedback loop circuit comprises:

an operational amplifier having a positive input, a negative input, and an output, said positive input of said operational amplifier being supplied with a DC reference voltage;

a first resistor connected between said AM demodulator and said negative input of said operational amplifier, whereby said demodulated signal is applied to said negative input of said operational amplifier through said first resistor;

a second capacitor having a first terminal and a second terminal, said first terminal of said second capacitor being connected to said negative input of said operational amplifier; and a second resistor having a first terminal and a second terminal, said first terminal of said second resistor being connected to said second terminal of said second capacitor, said second terminal of said second resistor being connected to the output of said operational amplifier, the output of said operational amplifier also being connected to drive said oscillator.

13. The improved reflected impedance telemetry system for use between an implantable medical device and an external transceiver, as set forth in claim 11, wherein said means for generating an information-containing magnetic field comprises:

a second inductor for transmitting said information-containing magnetic field;

a third capacitor connected in parallel across said second inductor;

a switch connected in parallel across said second inductor and said third capacitor; and means responsive to the information to be transferred in said information-containing magnetic field for periodically, sequentially opening and closing said switch to modulate a voltage across said second inductor and said third capacitor.

* * * * *

UNITED STATES PATENT AND TRADEMARK OFFICE
CERTIFICATE OF CORRECTION

PATENT NO. : 5,264,843
DATED : November 23, 1993
INVENTOR(S) : Sergiu Silvian

It is certified that error appears in the above-indentified patent and that said Letters Patent is hereby corrected as shown below:

In col. 6, line 30, delete "FIG. 1" and insert therefor --FIG. 2--.

In col. 8, line 10, delete "to the one side" and insert therefor --to one side--.

In col. 10, line 42, in Claim 1, delete "occurs" and insert therefor --occur--.

Signed and Sealed this

Sixteenth Day of May, 1995

Attest:

BRUCE LEHMAN

Attesting Officer    *Commissioner of Patents and Trademarks*